United States Patent [19]

Walser

[11] 4,100,160
[45] Jul. 11, 1978

[54] THERAPEUTIC COMPOSITIONS COMPRISING ALPHA-HYDROXY ANALOGS OF ESSENTIAL AMINO ACIDS AND THEIR ADMINISTRATION TO HUMANS FOR PROMOTION OF PROTEIN SYNTHESIS AND SUPPRESSION OF UREA FORMATION

[75] Inventor: Mackenzie Walser, Ruxton, Md.

[73] Assignee: The Johns Hopkins University, Baltimore, Md.

[21] Appl. No.: 669,588

[22] Filed: Mar. 23, 1976

Related U.S. Application Data

[63] Continuation-in-part of Ser. No. 461,259, Apr. 15, 1974, abandoned, and Ser. No. 461,260, Apr. 15, 1974, abandoned, each is a continuation-in-part of Ser. No. 355,326, Apr. 30, 1973, abandoned, and Ser. No. 355,327, Apr. 30, 1973, abandoned, said Ser. No. 355,327, is a continuation-in-part of Ser. No. 270,986, Jul. 12, 1972, abandoned.

[51] Int. Cl.² .................. A61K 31/19; A61K 31/40; A61K 31/195
[52] U.S. Cl. ................................. 424/274; 424/317; 424/319
[58] Field of Search ..................... 424/274, 317, 319

[56] References Cited

U.S. PATENT DOCUMENTS

| 2,457,820 | 1/1949 | Howe et al. | 424/319 |
| 3,764,703 | 10/1973 | Bergström | 424/319 |

OTHER PUBLICATIONS

Chemical Abstracts 81:54452q (1974).
Chemical Abstracts 82:144958j (1975).
Richards et al., Lancet, pp. 128-134, (Jul. 17, 1971).
Richards et al., Lancet pp. 845-849, (Oct. 21, 1967).
Rudman, J. of Clinical Invest. 50, pp.90-96, (1971).
Parthasarathy et al., Canad. J. of Biochem., vol. 42, 1964 pp. 377-384.

*Primary Examiner*—Leonard Schenkman
*Attorney, Agent, or Firm*—Seidel, Gonda & Goldhammer

[57] ABSTRACT

Compositions containing the hydroxy analogs of certain essential amino acids are formulated for therapeutic use, particularly in the treatment of renal disorders, hepatic failure and conditions of protein wasting in human subjects. In preferred embodiments, keto analogs of certain essential amino acids are used in combination with hydroxy analogs of other essential amino acids.

30 Claims, 1 Drawing Figure

THERAPEUTIC COMPOSITIONS COMPRISING ALPHA-HYDROXY ANALOGS OF ESSENTIAL AMINO ACIDS AND THEIR ADMINISTRATION TO HUMANS FOR PROMOTION OF PROTEIN SYNTHESIS AND SUPPRESSION OF UREA FORMATION

STATEMENT OF GOVERNMENT INTEREST

The invention described herein was made in the course of work under a grant or award from the Department of Health, Education and Welfare.

CROSS-REFERENCE TO RELATED APPLICATIONS

This patent application is a continuation-in-part of prior U.S. patent applications Ser. Nos. 461,259 and 461,260 both filed Apr. 15, 1974 and now abandoned, each of which being a continuation-in-part of U.S. patent applications Ser. Nos. 355,326 and 355,327 each filed Apr. 30, 1973 and now abandoned; said application Ser. No. 355,327 being a continuation-in-part of now abandoned U.S. patent application Ser. No. 270,986 filed July 12, 1972.

BACKGROUND OF THE INVENTION

A. Field of the Invention

The invention generally relates to a therapeutic composition of matter and method for administering said composition to human beings. Particularly, the several embodiments of the invention provide for treatment of renal disorders, such as uremia, for treatment of hepatic diseases, such as hyperammonemia and portal-systemic encephalopathy, for alleviating the effects of protein wastage and, in certain embodiments thereof, for altering metabolic pathways in order to prevent leakage of nitrogen from the body's metabolic pool.

B. Description of the Prior Art

Prior art treatment of the several bodily disorders to which the present invention finds application varies according to the particular disorder, this variation resulting in certain instances from a lack of understanding of the metabolic processes involved in the respective situations. Other than dialysis, prior art treatments applicable to renal disorders, such as uremia, center around replacement of amino acids lacking in the individual suffering from said disorder. In such a situation, nitrogenous wastes resulting from the normal breakdown of amino acids in the body are not adequately excreted and accumulate in the blood. Due to the inability to excrete these wastes, ingestion of protein must be restricted, thereby resulting in amino acid deficiencies. One particular treatment disclosed by Howe et al. in U.S. Pat. No. 2,457,820 provides for administering certain essential amino acids to correct this protein deficiency without overburdening the remaining kidney function.

Bergstrom et al. in U.S. Pat. No. 3,764,703 discloses a mixture of eight essential amino acids optionally combined with either or both L-arginine and L-histidine (which the patent calls "semi-essential" amino acids) for treatment of uremic conditions caused by renal insufficiency. However, the provision of additional amino acids in the blood stream often results in overburdenment of the kidney function, especially in severe cases, due to the resulting breakdown of the introduced amino acids into excessive nitrogenous wastes. Furthermore, these compounds are highly unpleasant to taste. For a comparison of results of essential amino acid therapy as opposed to that employing essentially the compositions of the present invention, see Walser et al. (1973), *Journal of Clinical Investigation*, 52:679. Also, Walser, M., (1975) "Keto-acids in the Treatment of Uremia", *Clinical Nephrology*, 3:80.

Other workers studying renal failure have suggested the dietary use of keto-acid analogs of amino acids and have proposed but have not demonstrated the use of keto-analogs of a combination of certain essential amino acids as a therapeutically beneficial treatment for uremia. These prior suggestions have been based on the assumption that such keto-acid analogs might combine with ammonia derived from urea breakdown in the intestines. Subsequently, such suggestions relating to keto-acid usage have been discounted. See editorial in *The Lancet*, Aug. 2, 1975, page 214. The present invention reveals that urea breakdown, and thus a high blood urea concentration, is not a prerequisite to efficacy of these analogs. On the contrary, low blood urea levels facilitate efficacy and can be maintained for months despite severe renal insufficiency.

The work resulting in the present invention has demonstrated the value of the use of combinations of hydroxy-acid analogs and keto-acid analogs of amino acids as a medicinal treatment for these disorders. The use of these combinations according to the invention diverts nitrogen away from urea formation, this nitrogen now being known to derive from body metabolic processes themselves. Thus, a particular object of the invention is to suppress urea formation and, in so doing, to minimize urea accumulation in body fluids, as well as nitrogen loss in the urine as urea.

Prior art treatment of hepatic failure such as is characterized by hyperammonemia and portal-systemic encaphalopathy is generally based on attempts to reduce the production of ammonia in the intestines and to restrict dietary protein. Individuals suffering from the aforementioned disorders are commonly deficient in protein owing to their intolerance of dietary protein; therefore, treatment according to the present invention provides for the reduction of ammonia in the bloodstream while simultaneously promoting protein synthesis.

Protein depletion due to dietary deficiency or excessive nitrogen losses may be treated by introduction of adequate protein to the diet. The present invention may also be used, and often with greater efficacy, to reduce protein requirements by diverting nitrogenous precursors in the body away from urea formation (urea is normally excreted, resulting in bodily nitrogen loss). This nitrogenous precursor diversion results in essential amino acid formation in the body by combination of the precursors not only with the keto-acids of the present combination but also the keto-acids formed by bodily enzymatic activity on the hydroxy-acid analogs in the combinations which are introduced into the body. The body's mechanisms for conserving protein can also be altered by administration of these combinations of hydroxy-acid analogs and keto-acid analogs of these amino acids. Thus, losses of nitrogen from the body can be diminished whether caused by malnutrition, cancer, diabetes, surgery, or any other wasting disease or condition which caused loss of body tissues. A positive nitrogen balance may be attained according to the invention by oral or parenteral administration of the present compositions of matter to reduce nitrogen wastage from the body.

SUMMARY OF THE INVENTION

The present invention provides compositions of matter and methods for promoting protein synthesis and suppressing urea formation in the human body, certain embodiments thereof being applicable to therapeutic treatment of both renal and hepatic disorders, to treatment of protein deficiencies, and to prevention of nitrogen wastage from the body.

The compositions employed in practice of the present invention comprise hydroxy-acid analogs and keto-acid analogs of certain essential amino acids or salts of the acid analogs. Oral or intravenous administration of these analogs acts as a treatment for renal failure by promoting protein synthesis in the blood stream, thereby resulting in suppression of urea breakdown which correspondingly reduces the tendency of the liver to form urea. Contrary to the prior art prediction that a high urea breakdown rate would facilitate the use of keto-acids in the body, the present invention demonstrates that urea breakdown is not a necessary factor governing the effective use of the proposed analogs of essential amino acids. The reduction of urea breakdown tends to reduce the net rate of urea-nitrogen appearance in the body, thus minimizing the rate of urea formation by the liver. Accordingly, renal disorders, such as uremia, may be controlled in certain instances without dialysis or as a supplement thereto.

The successful treatment of renal failure with the proposed analogs of essential amino acids also occurs due to the fact that the body's mechanisms for conserving protein are altered by their introduction into the body. Normal metabolic pathways are altered such that leakage of nitrogen from the body's metabolic pool is reduced by administration of these analogs into the body. This alteration of metabolic processes occurs when nitrogen intake is reduced to a low level and these analogs are administered. Thus, endogenous amino acids are more efficiently re-utilized in the treatment of renal failure as well as in the treatments described hereinafter for treatment of hepatic disorders and for dietary protein deficiencies.

Treatment of hepatic disorders through the use of the present invention also calls for the effective suppression of urea formation in the body due to the combination of nitrogen-containing urea precursors, such as ammonia, with keto-acids administered as such or formed by enzymatic oxidation in the body of the hydroxy-acid analogs of certain essential amino acids.

These processes result, for example, both in the formation of essential amino acids in normal muscle tissue and in the reduction of ammonia in the bloodstream, both being highly desirable objects in the treatment of hepatic disorders. This synthesis in normal muscle tissue as now understood provides a basis for use of the present invention as a treatment for hepatic disorders wherein the liver is incapable of performing such a metabolic function.

The invention is further applied to treatment of protein deficiencies by reducing protein requirements. Conversion of the keto-acid analogs of certain essential amino acids administered or formed in the body from their corresponding hydroxy analogs suppresses urea formation by diverting nitrogenous precursors of urea away from urea formation through combination of said precursors with the keto-acids to form amino acids. Urea formed in the body is normally excreted, thereby resulting in a systematic loss of elementary protein components. Reduction of this loss of urea coupled with conversion of said nitrogenous urea precursors to available amino acids allows bodily conservation of protein without toxic effects. The "turning off" of the body's mechanisms for leaking nitrogen from the body's metabolic pool assists in maintaining nitrogen balance.

It is therefore an object of the invention to provide a composition of matter and a method for promoting protein synthesis, suppressing urea formation, and reducing nitrogen leakage from the metabolic pool in the human body.

It is another object of the invention to provide a therapeutic treatment for renal disorders and for dietary protein deficiencies.

It is a further object of the invention to administer the hydroxy-acid analogs and keto-acid analogs of certain essential amino acids to individuals suffering from renal or hepatic disorders, and dietary protein deficiencies in order to mitigate the symptomatic responses of said individuals.

A still further object of the invention is the prevention of the wasting of body nitrogen during periods of low nitrogen intake or nitrogen wastage by alteration of the body's mechanisms for conserving protein.

Further objects and attendant advantages of the invention will become more readily apparent from the following detailed description of the preferred embodiments of the invention.

DESCRIPTION OF THE PREFERRED EMBODIMENTS

The present compositions of matter and methods relative to their use generally depend in the several embodiments thereof on the promotion of protein synthesis and suppression of urea formation in the body. The present invention embodies the now realized need to minimize rather than accelerate the breakdown of urea in the human gut during treatment of renal failure, hepatic disease, and dietary protein deprivation. The invention particularly comprises a composition of matter including as constituents thereof the hydroxy-acid analogs of certain essential amino acids.

Use of the present invention, for example, causes alteration of the body's mechanisms for conserving protein and prevents nitrogen loss from the body's metabolic pool.

The present composition of matter generally comprises certain of the hydroxy-acid analogs of the amino acids listed in the left-hand column of Table I below. The right-hand column of Table I lists for convenience the proper names for the hydroxy-acid analogs of the essential amino acids including that of histidine and arginine.

Table I

| Amino Acid | Hydroxy-Acid Analog |
|---|---|
| Valine | Alpha-hydroxy-isovaleric acid |
| Leucine | Alpha-hydroxy-isocaproic acid |
| Isoleucine | Alpha-hydroxy-beta-methylvaleric acid |
| Methionine | Alpha-hydroxy-gamma-methylthiobutyric acid |
| Phenylalanine | Alpha-hydroxy-beta-phenylpropionic acid (Phenyl lactic acid) |
| Histidine | Alpha-hydroxy-beta-imidazolepropionic acid |
| Tryptophan | Alpha-hydroxy-beta-indolepropionic acid |

Table I-continued

| Amino Acid | Hydroxy-Acid Analog |
| --- | --- |
| Threonine | Alpha-hydroxy-beta-hydroxybutyric acid |
| Arginine | Alpha-hydroxy-gamma-guanidinovaleric acid |
| Lysine | Alpha-hydroxy-gamma-aminocaproic acid |

Various combinations of the hydroxy-acids listed above may be administered in combination with keto-acids to be named hereinafter either orally or parenterally as the acid analogs per se or as salts thereof, preferably as the sodium or calcium salts, those individuals having a tendency to retain sodium being better treated with the calcium salts. Intravenous administration of these hydroxy-acids and/or the keto acids may often be more effective in severe instances of renal or hepatic disease or for individuals incapable of oral ingestion of medication. The L-hydroxy acids are preferably used in the invention due to their more effective conversion by bodily enzymes to the corresponding keto-acids of the respective amino acids except for the hydroxy analog of methionine, which is given as the D, L-form. In addition, best results are usually obtained when the hydroxy-acid and/or keto acid analogs of valine, leucine, and isoleucine are each present in about one and a half to three times (by weight) of the amounts of the analogs of methionine and phenylalanine (corresponding to about two to three times on an equal molar basis).

As heretofore indicated, certain of the hydroxy-acids listed in Table I may be replaced with the several alpha-keto-acid analogs of the same essential amino acids. In Table II below, the right-hand column lists the proper names for the corresponding keto-acid analogs of the amino acids listed in the left column.

Table II

| Amino Acid | Keto-Acid Analogs |
| --- | --- |
| Valine | Alpha-ketoisovaleric acid |
| Phenylalanine | Phenylpyruvic acid |
| Methionine | Alpha-keto-gamma-methylthiobutyric acid |
| Leucine | Alpha-ketoisocaproic acid |
| Isoleucine | Alpha-keto-beta-methylvaleric acid |
| Histidine | Imidazolepyruvic acid |
| Tryptophan | Indolepyruvic acid |
| Lysine | Alpha-keto-gamma-aminocaproic acid |
| Threonine | Alpha-keto-beta-hydroxy butyric acid |
| Arginine | Alpha-keto-gamma-guanidinovaleric acid |

Methods of preparing both the hydroxy-acid and keto-acid analogs of the amino acids listed are well known. The hydroxy acids are conveniently prepared by reacting the corresponding amino acid with nitrous acid.

The present invention primarily involves in preferred embodiments thereof the administration into the body of certain combinations of the hydroxy-acid analogs of Table I and of the keto-acid analogs of Table II. In the present compositions of matter and in the methods relative to the use thereof, either the hydroxy-acid analog or the keto-acid analog of any one amino acid is used in a combination, i.e., if the hydroxy-acid analog of any one amino acid is present in a mixture, then the keto-acid corresponding to that amino acid need not be present in the mixture.

Mixtures of these hydroxy-acids and keto-acids are advantageous in that certain mixtures are more palatable, more stable, often less expensive, and more effective than the hydroxy-acids alone. These mixtures also prove more palatable and less expensive than the keto-acids alone.

Certain hydroxy-acid analogs prove less expensive than the keto-acid analog of the corresponding amino acid. The hydroxy-acid analogs of methionine, phenylalanine and isoleucine are most effective in the body. The hydroxy-acid analog of valine proved least effective, so that the keto-acid analog of valine is employed instead of the hydroxy-acid analog thereof in the preferred combinations of the present invention.

The hydroxy-acid and/or keto-acid analogs of the first five listed amino acids of Table I are most readily available at reasonable costs. Accordingly, the last five listed amino acids when used in any of the several embodiments of the present composition of matter are generally employed in amino acid form as such.

In the treatment of renal disorders, particularly, L-histidine is preferably included in the administered therapeutic composition. While the necessary presence of arginine has not presently been established in the treatment of renal disorders, its inclusion is not contraindicated, and may be desirably included in compositions for treatment of certain types of hyperammonemia in children and other hepatic conditions in adults.

In one embodiment of the invention found to be economically attractive while retaining therapeutic viability, the sodium or calcium salts of the hydroxy-acid analogs of methionine, phenylalanine, and isoleucine, as previously listed, are administered either orally or intravenously along with the amino acids for which the hydroxy-acid analogs are not readily available at the present time, i.e., L-tryptophan, L-threonine, L-lysine, and either or both L-histidine and L-arginine; and with the sodium or calcium salts of the alpha-keto analogs of valine and leucine. The administered compounds are given in an amount equal at least to from one to one and a half times the minimal daily amount of the corresponding amino acid (or of the amino acid itself) ordinarily required by the individual undergoing treatment. The respective mixtures of the compounds which form the several preferred embodiments of the invention, particularly those compounds used to treat renal disorders, may be administered in four identical daily doses. Of course, the dosage of individual components of the invention can be modified if analysis of the user's blood for the corresponding amino acids reveals an abnormal balance.

Since the present invention may be practiced in the treatment of several bodily disorders in which protein synthesis and urea suppression play important therapeutic roles, it is desirable to consider these treatments individually in order to more clearly define the respective embodiments of the invention. The following description is thus divided into subject areas relating to the bodily disorders for which the invention finds therapeutic application. A discussion of the alteration of the body's mechanisms for conserving protein is also given, it being understood that this alteration acts to produce the effects noted in the treatment of the several disorders discussed herein.

Treatment of Renal Disorders

In the human body, nitrogenous waste is produced from the breakdown of protein and amino acids. These wastes are normally excreted by the kidneys. If kidney function becomes deficient, nitrogenous wastes accumulate to toxic levels in bodily fluids, resulting in a disease known as uremia. Restriction of dietary protein reduces waste accumulation but may result in a negative nitrogen balance which progressively depletes bodily stores of protein. Exogenous protein may be supplemented (inadequately) by amino acids administered orally or parenterally. Even with such treatment, the end-products of nirogen metabolism, primarily urea, continue to accumulate due in part to the breakdown of the exogenous amino acids themselves.

According to one embodiment of the invention, keto-acid analogs of valine and leucine may be administered together with the hydroxy-acid analogs of methionine, isoleucine and phenylalanine; histidine, tryptophan, lysine, and threonine may be administered either as such or, if available, in the form of their hydroxy analogs. Oral or intravenous administration produces an improved symptomatic response in an individual suffering from uremia.

Certain uremic individuals are unable to eat or take oral medication. Accordingly, parenteral nutrition must be provided. Previously, solutions of amino acids were administered intravenously. As described, however, such treatment did not prove to be sufficiently effective. According to the present invention, the compositions described above may be administered intravenously in order to lower blood urea nitrogen, and therefore to reduce the severity of the uremic syndrome, by reducing urea formation through combination with urea precursors. Intravenous usage of the present composition is therefore particularly suited to the treatment of individuals suffering from severe uremia.

The daily requirements of the individual keto and hydroxy acid analogs of the mixture are preferably supplied in the form of their sodium or calcium salts, for oral or parenteral administration; the calcium salts being preferable in most cases of renal failure owing to sodium retention generally encountered in this condition. In the preferred practice, the prescribed total daily requirement is preferably administered divided into four identical aliquot doses. For parenteral administration, the prescribed daily requirement may be given at one time over a period of about 3 or 4 hours.

In the left column of Table III below, a practical minimum daily dosage range of the individual components of the mixture is set out, intended for administration to uremic patients of below average body weight (less than 50 kgs.) at the lower end of the disclosed range and to patients of higher than average body weight (above about 75 kgs.) at the upper end of the disclosed range. When individual idiosyncrasies are encountered, such as an abnormal balance of the corresponding amino acids in the patient's blood, the dosage of the individual components of the administered mixture can be modified.

Compositions falling within the ranges set out in Table III may be employed in oral as well as in parenteral administration. It has been observed that alpha-keto-isocaproic acid particularly is partially degraded by the intestines and furthermore that all three of the branched-chain keto acids are in fact partially degraded and relatively inefficiently aminated in the liver. Since the liver drains the blood from the intestines, it appears that higher quantities of these branched-chain keto analogs should preferably be employed in oral therapy than in intravenous administration, as for example, in amounts approaching the highr end of the range set out in Table III and in the order of up to about triple the amount of the other two keto analogues of the mixture.

It will be observed that the respective quantities of the components in the mixture tabulated below are based on using approximately one and a half to three times the equivalent quantities (by weight) of the branch chain amino acid anaogs (of valine, leucine and isoleucine) as compared to the quantities of the analogs of phenylalanine and methionine.

Table III

| Range gms | Substances | Specific Preferred Compositions | | |
|---|---|---|---|---|
| | | C | D | E |
| 2.0 – 4.0 | alpha-keto-isovalerate | 2.88 | 2.88 | 2.88 |
| 3.0 – 5.0 | alpha-keto-isocaproate | 4.00 | 4.00 | 4.00 |
| 2.5 – 3.5 | L-(R, S)-alpha hydroxy-beta methylvalerate | 0 | 0 | 2.92 |
| | or | | | |
| 2.5 – 3.5 | R, S-alpha-keto-beta-methylvalerate | 2.92 | 2.92 | 0 |
| 1.5 – 2.5 | D, L-alpha-hydroxy-gamma-methyl-thiobutyrate | 2.12 | 2.12 | 2.12 |
| 1.5 – 2.5 | phenylpyruvate | 2.00 | 0 | 0 |
| | or | | | |
| 1.5 – 2.5 | L-phenyllactate | 0 | 2.00 | 2.00 |
| ~0.25 ± 0.10 | L-tryptophan | 0.33 | 0.33 | 0.33 |
| ~0.5 – 0.7 | L-threonine | 0.67 | 0.67 | 0.67 |
| ~0.8 ± 0.10 | L-lysine hydrochloride | | | |
| | or | | | |
| | L-lysine acetate | 0.80 | 0.80 | 0.80 |
| ~0.5 ± 0..0 | L-histidine | 0.54 | 0.54 | 0.54 |

The specific preferred compositions are intended for persons of about average body weight. For adults of less than average body weight (50–75 kgs.), advocated dosages are at about the lower end of the disclosed range, while for adults above average body weight, dosages should generally be at about the upper end of the disclosed range. Adjustment of the quantity of any component of the mixture may be made as deemed necessary in the light of revealed idiosyncrasies, such as abnormal balance of the corresponding essential amino acids in the patient's blood. The indicated analogs are preferably administered as sodium or calcium salts, the latter being preferred in cases of sodium retention.

The following Table IV shows results in a subject with diabetic glomerulosclerosis. He was first treated with all nine essential amino acids at a total N intake of 4.5 g/day for a period of four months. During the last three days of this period, he was admitted for balance study. He was then changed to a mixture of five keto-analogs of essential amino acids plus the four remaining essential amono acids. Nitrogen balance became less negative and urea N appearance rate diminished. Renal function did not change. After one week, he was changed to a mixture containing the keto-analogs of valine and leucine, the D,L-hydroxy analog of methionine, and the L-hydroxy analogs of isoleucine and phenylalanine, as well as the four remaining essential amino acids (mixture E of Table III). Serum urea N fell further and nitrogen balance and urea nitrogen appearance remained at the same values as during keto-acid administration. Urea clearance actually increased significantly ($p < 0.05$). He was discharged home for 11 days. On readmission, both serum urea N and creatinine had risen and urea and creatinine clearances had fallen, reflecting progression of his underlying disease. However, nitrogen balance was now more strongly positive and urea nitrogen appearance rate was still very low. These results indicate the efficacy of this mixture in the management of this patient with severe chronic renal failure.

Table IV

| Treatment days | Serum Urea N mg% | Serum Creat mg% | Clearance Urea ml/min | Clearance Creat ml/min | N intake g/day | N balance g/day | Urea N appearance g/day |
|---|---|---|---|---|---|---|---|
| Amino acids 120–122 | 83 ±2 | 11.7 ±0.1 | 2.4 ±0.1 | 3.8 ±0.6 | 4.5 ±0.1 | −1.28 ±0.24 | 3.10 ±0.16 |
| Ketoacids 123–130 | 79 ±1 | 11.6 ±0.1 | 2.3 ±0.1 | 3.4 ±0.1 | 4.4 ±0.1 | −0.43 ±0.22 | 2.10 ±0.16 |
| Keto-hydroxy acid mixture 131–137 | 70* ±1 | 11.7 ±0.1 | 2.9# ±0.2 | 3.6 ±0.1 | 4.8 ±0.1 | −0.25 ±0.18 | 2.65 ±0.21 |
| Keto-hydroxy acid mixture 150–154 | 79* ±2 | 13.2* ±0.05 | 2.1 ±0.1 | 3.0# ±0.2 | 4.4 ±0.3 | ±0.72 ±0.37 | 2.27 ±0.16 |

*p < .01
p < .05

The efficacy of mixture D (Table III) is exemplified by the results of nitrogen balance studies conducted on five patients with severe chronic renal failure who were receiving a nearly protein-free diet (< 3 gm/day) plus mixture D (as calcium salts) plus enough glycine (a non-essential amino acid) to provide their nitrogen requirements. Under these experimental circumstances, valine, leucine, isoleucine, methionine, and phenylalanine are virtually absent from the diet except to the extent that they are provided as the analogs of these same amino acids in mixture D. Despite an average total nitrogen intake of only 4.31 gm per day, the patients were, on the average, in positive nitrogen balance on mixture D. These observations establish the efficacy of these analogs, administered by mouth as calcium salts, in replacing the corresponding amino acids, since nitrogen balance would be strongly negative in the dietary absence of any one of these five amino acids, as is well known. The nitrogen balances in these patients is reported in Table V.

Table V

Nitrogen balance in uremic patients receiving mixture "D" in association with a nearly protein-free diet

| Subj. | N intake, g/day Diet | 4EAA* | Glycine | Total | N output, g/day Urine | Stool | ΔUrea pool** | N balance, g/day |
|---|---|---|---|---|---|---|---|---|
| A. P. | 0.64 +019 | 0.39 ±0.00 | 1.75 ±0.19 | 2.78 ±0.05 | 2.46 ±0.16 | 0.96 ±0.05 | −0.11 | −0.53 ±0.14 |
| R. T. | 0.36 ±0.18 | 0.39 ±0.00 | 4.00 ±0.00 | 4.75 ±0.02 | 5.43 ±0.25 | 0.55 ±0.01 | −0.98 | −0.25 ±0.27 |
| L. R. | 0.52 ±0.03 | 0.39 ±0.00 | 3.83 ±0.17 | 4.69 ±0.16 | 2.57 ±0.14 | 0.60 ±0.01 | +0.87 | +0.65 ±0.18 |
| S. W. | 0.42 ±0.04 | 0.39 ±0.00 | 4.52 ±0.00 | 5.33 ±0.04 | 3.68 ±0.25 | 0.06 ±0.06 | +0.29 | +1.29 ±0.29 |
| P. C. | 0.51 ±0.03 | 0.39 ±0.00 | 3.50 ±0.00 | 4.01 ±0.03 | 2.49 ±0.13 | 0.85 ±0.12 | −0.40 | +1.07 ±0.16 |
| Ave. | 0.49 ±0.05 | 0.39 ±0.00 | 3.52 ±0.47 | 4.31 ±0.44 | 3.33 ±0.57 | 0.60 ±0.16 | −0.67 ±0.31 | +0.45 ±0.36 |

*N taken as L-threonine, L-histidine, L-lysine . HCL and L-tryptophan
**Change in body urea nitrogen pool, calculated from serum urea N concentration and weight
Values shown are means ± S. E. M.; study periods averaged one week.

A patient with chronic glomerulo-nephritis of many years duration, had undergone hemodialysis once or twice weekly for 5 months. He was treated with mixture C (Table III) for a total of 14 months. During this period, no deterioration of renal function has been detected and he has remained virtually asymptomatic.

Nitrogen balance studies were conducted in six severely uremic patients totalling 73 patient days. The results are reported in Table VI below. These individuals were receiving mixture C (Table III) with an average net nitrogen intake, defined as total nitrogen intake minus urinary protein nitrogen, of 2.91 grams per day. On this intake, patients with chronic renal failure may be expected to have a negative nitrogen balance amounting to greater than 2.00 grams per day when receiving merely protein restriction and a negative nitrogen balance of approximately 1.50 grams per day when receiving essential amino acids as such. As shown in Table VI, the average nitrogen balance in these subjects receiving mixture C averaged about −1.03 grams per day. It should be noted that these subjects were receiving somewhat less dietary protein than that necessary to meet their individual requirements. This study demonstrates the efficacy of this mixture, since demonstration of positive nitrogen balance can only be successfully carried out in individuals who are protein depleted; non-protein depleted subjects will not show positive nitrogen balance regardless of how much protein is administered.

Table VI

Nitrogen balance in severely uremic patients receiving mixture C and restricted diet protein

| Subject | Days | Net N intake* g/day | N balance g/day |
|---|---|---|---|
| SA | 12 | 2.20 | −1.82 |
| SA | 16 | 3.43 | −0.67 |
| LD | 5 | 0.83 | −2.96 |
| LM | 13 | 4.18 | −1.66 |
| LM | 11 | 3.87 | −0.51 |
| JS | 8 | 2.84 | +0.55 |
| JS | 5 | 1.98 | −0.54 |
| CW | 3 | 3.91 | −0.68 |
| Total | 73 | Mean 2.91 ±0.41 | −1.03 ±0.38 |

*Total N intake minus urinary protein nitrogen

Figure 1:
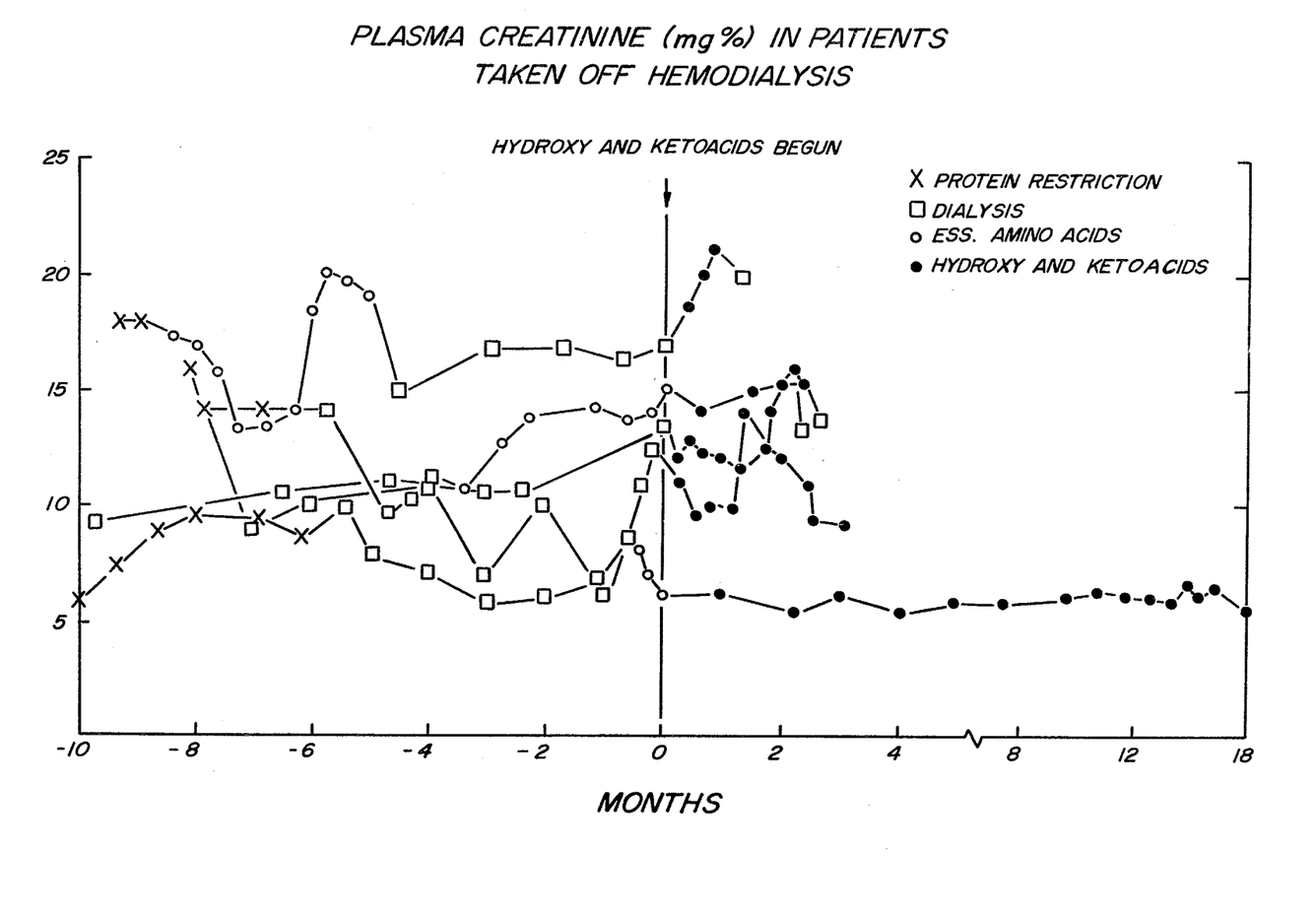
The accompanying drawing is a graph showing the plasma creatinine levels in patients suffering from chronic renal failure, when taken off hemodialysis.

It was previously established that serum creatinine concentration effectively measures remaining renal function in patients having renal disorders. A high serum creatinine level is indicative of severe renal insufficiency. The serum creatinine level is lowered by regular hemodialysis, as is illustrated in the curves to the left of the vertical line in the graph, when these patients were on protein restriction or receiving essential amino acids as such (prior to beginning therapy with the analogs). Had these patients not been undergoing hemodialysis or if hemodialysis was discontinued, creatinine levels would be expected to rise sharply during the ensuing week or two and severe symptoms would develop.

These patients were subsequently taken off dialysis and treated with a mixture of calcium salts of the keto and hydroxy analogs of five of the essential amino acids and four essential amino acids as such, corresponding to mixture D of Table III. (One of these patients, shown in the lowermost curve, was treated with mixture C of Table III for approximately fourteen months, followed by mixture D thereafter.) In only one instance (uppermost curve) was there a rise in creatinine level, although not very sharp, when the patient was taken off of hemodialysis and he was returned to dialysis after a few weeks. All the other patients, however, showed significant and unexpected results as to the effect of the treatment with the amino acid analog mixtures, in that the plasma creatinine did not rise with time as expected, and in some cases actually fell despite discontinuance of dialysis. These results indicate that the treatment with the administered acid analog mixtures of the invention produces a substantial and in many cases prolonged improvement in renal function despite long-standing renal insufficiency. The longest period in which a patient remained off of dialysis in this study is that shown in the lowermost curve. Although the graph stops at 18 months, this patient has now been on analog therapy for more than 22 months.

It should be noted that the patients considered in the foregoing studies have remained virtually asymptomatic while off dialysis. The criterion used in these studies for returning a patient to dialysis was the same as that generally used to first place a patient in dialysis.

For intravenous administration, a solution of the composition is prepared by first dissolving the sodium salt of phenylpyruvic acid or the corresponding lactate in 50 ml. of distilled water with the aid of warming, and then adding the remaining components of the mixture to the resulting solution. Solution of all the substances being thus accomplished, the solution is sterilized by Millipore filtration, and tested for sterility and pyrogenicity. The solution is frozen until use. When used, the solution is thawed to room temperature and diluted to between 250–400 ml. with sterile, pyrogen-free water. The isotonic solution thereby resulting has a neutral pH and is satisfactory for intravenous use. The solution is stable for at least 8 hours (and longer) at room temperature. Intravenous administration of the solution is usually accomplished over a 3 to 4 hour period. In certain situations, more than one infusion may be given daily.

Since the hydroxy-acids in the composition thus administered into the body are believed to be converted by bodily enzymatic activity to the corresponding keto-acids, it can be understood that treatment according to the present invention may be effectively used also in combination with additional attempts to reduce urea breakdown in the body, thereby to minimize the rate of urea formation by the liver.

A palatable combination of hydroxy-acids and keto-acids which retains therapeutic viability for treatment of renal failure as well as for the other disorders and conditions discussed here can also be administered orally in juices or salt-free bullion or in gelatin capsules.

The effectiveness of the racemic hydroxy analog of methionine in patients with severe chronic renal failure is illustrated in Table VII below. These patients were initially treated during the indicated period shown in the table with a mixture of the nine essential amino acids to supplement dietary protein. In a subsequent period, the same patients were changed over to a mixture of calcium salts of the keto analogs of valine, leucine, isoleucine and phenylalanine with the calcium salt of D,L-alpha-hydroxy-gamma-methyl-thiobutyric acid and the other four essential amino acids, supplementing an inadequately low protein diet. It will be seen from the table that the mean fasting methionine levels as a rule were appreciably higher when the racemic hydroxy analog of methionine was administered as compared to methionine contained in the administered mixture of the nine essential amino acids as such. In the two reported cases in which the mean level of methionine did not increase by the change to the hydroxy analog, the latter had been administered only over a short period of several days.

Table VII

Fasting plasma methinine levels [met] during administration of calcium D,L-alpha-hydroxy-gamma-methylthiobutyrate (MGA) in conjunction with a ketoacid-amino acid mixture plus an inadequately low protein diet in patients with severe chronic renal failure

| Subj. | Serum creatinine mg/100 ml | Dietary protein gm/day | Days prior therapy | Prior mean [met] $\mu M$ | Days of MHA therapy | Mean [met] $\mu M$ | Change in [met] $\mu M$ |
|---|---|---|---|---|---|---|---|
| Patients on prior therapy with nine essential amino acids | | | | | | | |
| Ca. W. | 8 | 19 | 9 | 30 | 3 | 26 | −4 |
| G. Mc. | 8 | 16 | 25 | 32 | 3 | 31 | −1 |
| E. P. | 14 | 19 | 31 | 33 ±3 | 14 | 39 | +6 |
| Ch. W. | 16 | 18 | 104 | 22 ±1 | 16 | 25 ±1 | +3 |
| E. Mc. | 14 | 24 | 4 | 24 | 10 | 26 | +2 |
| L. M. | 7 | 19 | 3 | 31 | 25 | 37 ±2 | +6 |
| C. H. | 15 | 11 | 65 | 35 | 36 | 37 | +1 |
| Mean | 8.2 | 18 | 29 | 30 | 15 | 32 | +2 |
| S.E.M. | ±0.6 | ±1 | ±16 | ±2 | ±5 | ±2 | ±1 |

Treatment of Hepatic Disorders In Adults

Hepatic disorders, such as are characterized by hyperammonemia and portal-systemic encephalopathy, have previously been treated by attempts to reduce intestinal ammonia release, since the high peripheral blood ammonia present in these conditions is believed responsible for the symptoms of the disorders. Protein restriction is commonly required, also. Usual treatment consists of reducing the bacterial flora of the intestine by oral administration of poorly absorbed antibiotics, such as neomycin. The disorder known as portal-systemic encephalopathy, a condition in which the portal circulation draining the intestines abnormally communicates with the systemic circulation, results in passage of ammonia into the systemic circulation with resulting changes in cerebral and nervous function.

Thus, ammonia accumulates in the blood rather than being converted to urea in the liver as would normally occur. Individuals suffering from this disorder have defective liver functions and cannot tolerate protein. Again, prior treatment centers on attempts to reduce the production of ammonia in the intestines by means of antibiotics, lactulose, or cathartics. Although it is now believed that these individuals generally suffer from protein deficiencies, the administration of amino acids has been contraindicated due to the extra load of ammonia produced by the eventual breakdown of the amino acids.

The present invention provides an effective treatment for these hepatic disorders by promoting utilization of the circulating ammonia in protein synthesis, thereby leading to a partial correction in protein deficiency. Also, the body's mechanisms for producing urea are altered and thus conserve protein. Thus, blood ammonia is reduced with resulting symptomatic relief by virtue not only of the combination of nitrogen-containing urea precursors, such as ammonia, with the keto-acid analogs of amino acids, formed from the administered hydroxy analogs or given as such, but also due to the alteration of the body's mechanisms for conserving protein. Essential amino acids are formed which tend to correct the nutritional disturbance while reducing the toxic effects of ammonia within the circulation.

This particular embodiment of the present composition of matter comprises the hydroxy analog of methionine with one or more of the hydroxy-acid analogs of leucine, isoleucine and phenylalanaine. As a practical matter, the availability of the corresponding hydroxy-acid analogs of their amino acids usually necessitates the usage of L-tryptophan, L-threonine, L-lysine monohydrochloride, and L-arginine in formulations employing these components. Additionally, the sodium or calcium salts of alpha-keto-isovaleric acid and alpha-keto isocaproic acid are used in the preferred compositions.

It should be noted here, for example, that this embodiment of the present composition of matter differs from the embodiment previously described for treatment of renal disorders only in the inclusion of arginine. This embodiment of the present composition of matter may be administered orally as a mixture in juices or salt-free beef boullion, or in gelatin capsules. A solution suitable for intravenous administration may be prepared as previously described relative to the preparation of the mixture used for intravenous treatment of renal disorders. Oral or intravenous dosages could be administered from one to three times daily. Practical ranges of a composition for treatment of hepatic disorders in adults may be that set out in Table III, left column with addition thereto of about 1 to 4 grams of L-arginine. In general, however, somewhat wider ranges of the individual components may be employed to cover specific needs of various hepatic patients, who may exhibit excesses of methionine, phenylalanine, and tryptophan.

In Table VIII below, a practical range of the individual components of the mixture is set out, intended for administration to adult hepatic patients of below average body weight (less than 50 kgs.) at the lower end of the disclosed range and to patients of above average body weight (above about 75 kgs.) at the upper end of the disclosed range. When individual idiosyncrasies are encountered, such as abnormal balance of the corresponding amino acids in the patient's blood, the dosage of the individual components of the administered mixture can be modified.

Table VIII

| Quantity | Substance |
|---|---|
| 3 – 6 grams | alpha-keto-isovalerate |
| 3 – 7 grams | alpha-keto-isocaproate |
| 3 – 6 grams | L-(R, S)-alpha hydroxy-beta-methyl-valerate or R, S-alpha-keto-beta-methyl valerate |
| 0 – 2 grams | D,L-alpha-hydroxy-gamma-thiobutyrate |
| 0 – 3 grams | phenylpyruvate or phenyllactate |
| 0 – 0.2 gram | L-tryptophan |
| 0.5 – 1.0 gram | L-threonine |
| 0.8 – 1.5 gram | L-lysine hydrochloride or acetate |
| 1 – 4 grams | L-arginine |
| 0.4 – 0.8 gram | L-histidine |

The keto and hydroxy analogs ae preferably administered as sodium or calcium salts.

The small amount of protein included in the patient's regular diet may furnish the needed amount of histidine. If so, inclusion of L-histidine in the above formulation (Table VIII) may be omitted if analysis of the patient's blood indicates adequate presence of histidine.

Treatment with the compositions thus described results in an increase in those essential amino acids which are deficient in and a reduction in blood ammonia levels. The neurological status of the individuals so treated also improves. However, these effects are transient, thereby requiring daily treatment.

The favorable response of patients suffering from hepatic disorders to the treatment according to the invention can be attributed in part from promoting protein synthesis in the body and from the lowering of blood ammonia. Conversion of the keto-acids to the corresponding amino acids can be shown to occur in normal muscle tissue and results in relief of symptomatic responses due to high blood ammonia and to partial correction of protein deficiency. These desirable results are due to combination of nitrogen-containing urea precursors, such as ammonia, in the blood with the administered keto-acids or formed in the body by enzymatic activity on the hydroxy-acids introduced in the body according to the invention. A discussion of the effects of the alteration of the body's mechanisms for conserving protein, which effects apply inter alia to the treatment of the several disorders including hepatic disorders described herein, will be given hereinafter.

Keto And Hydroxy Acid Therapy In Congenital Hyperammonemia

Congenital disorders caused by defects in each of the five enzymes of the Krebs-Henseleit urea cycle have been previously described in the literature. The clinical and biochemical manifestations differ somewhat among these syndromes, but all are characterized by hyperammonemia, imparied mental and physical development, and episodes of vomiting, lethargy, and coma after the ingestion of protein. Hyperammonemia is most pronounced in patients with defects of the first two enzymes of this cycle: carbamyl phosphate synthetase and ornithine transcarbamylase.

Treatment of these disorders is unsatisfactory, and most children die in infancy. Protein restriction ameliorates symptoms but does not restore the ammonia concentration of plasma to normal and may prevent adequate growth.

In an article reported by the present applicant and his associates appearing in Batshaw, M. et al. (1975) *New England Journal of Medicine*, 292:1085, a case is reported of a 13-year-old girl with a carbamyl phosphate synthetase deficiency treated with alpha-keto analogs of five essential amino acids: valine, leucine, isoleucine, methionine and phenylalanine. This approach was attempted because of previous observations made in the cases of adults with hyperammonemia and portal-systemic encephalopathy caused by cirrhosis of the liver. It was reasoned that these five keto analogs of the essential amino acids might become incorporated into protein and thereby promote growth and reduce hyperammonemia because of transamination to the corresponding amino acids.

The results indicated that after intravenous infusion of the keto analogs administered the corresponding plasma amino acids, including alloisoleucine and tyrosine, rose sharply. Twenty-four hours later, fasting plasma ammonia had fallen from the pre-infusion value of 0.050 to 0.028mM. Protein intake was kept at 0.5 g/kg for 2 weeks. Addition of keto acids by mouth reduced plasma ammonia and alanine to normal or near normal levels. Seizures and episodes of vomiting and lethargy decreased in frequency. Urinary nitrogen decreased, suggesting that nitrogen balance improved. These data indicated that keto acids could be useful in the treatment of congenital hyperammonemia.

During the course of the treatment, numerous adjustments in the composition of the mixture were made. Eventually, normal levels of plasma ammonia and most amino acids were achieved, with three exceptions: slightly increased glutamine, pronounced alloisoleucinemia and persistently low phenylalanine. Alloisoleucine was shown not to be incorporated into plasma protein and not to be excreted in the urine; hence this abnormality was viewed as being clinically insignificant. Compared to the pretreatment period, her clinical status improved markedly. Temporary withdrawal of the supplements led to prompt increases in plasma ammonia, glutamine and alanine. From these observations, we concluded that this therapy provided safe and effective long-term management for this patient's disorder and would be useful in other cases of congenital hyperammonemia.

This patient was subsequently studied over a longer period of intermittent therapy using analogs of the essential amino acid supplemented with the essential amino acids as such under moderate protein restriction.

Whereas in the earlier treatment, only the keto analogs of the five essential amino acids were administered, in the present study various combinations of the keto analogs with and without other essential amino acids were employed. In certain of these compositions, the D,L hydroxy analog of methionine was substituted for the corresponding keto analog. Various compositions employed are shown in Table IX.

TABLE IX

| Mix | Analogues (gm of Ca or Na salt) | | | | | | | | L-Amino Acids (gm) | | |
|---|---|---|---|---|---|---|---|---|---|---|---|
| | val | leu | ile | phe | met | phe | his | try | lys HCl | arg HCl | thr |
| G | 1.44* | 1.94* | 1.46* | 4.00* | 2.12* | 0 | 0 | 0 | 0 | 0 | 0 |
| H | 1.44* | 1.94* | 1.32* | 4.00* | 2.12# | 0 | 0 | 0 | 0 | 0 | 0 |
| I | 1.44* | 1.94* | 1.32* | 4.00* | 2.12# | 0 | 0.22 | 0.125 | 0.81 | 0.66 | 0.48 |
| J | 1.44* | 1.94* | 0.66* | 4.00* | 2.12# | 0 | 0.22 | 0.125 | 0.81 | 0.66 | 0.48 |
| K | 1.44* | 1.94* | 1.32* | 4.00* | 2.12# | 0 | 0.22 | 0.125 | 0.81 | 0 | 0.48 |
| L | 1.44* | 1.94* | 1.32* | 4.00* | 2.12# | 0 | 0.22 | 0.125 | 0.81 | 0.66 | 0.48 |
| M | 1.44* | 1.94* | 1.32* | 0 | 2.12# | 1.65 | 0.22 | 0.125 | 0.81 | 0.66 | 0.48 |
| N | 1.44* | 1.94* | 1.32* | 4.00+ | 2.12# | 0 | 0.22 | 0.125 | 0.81 | 0.66 | 0.48 |
| O | 1.44* | 1.94* | 1.32* | 4.00+ | 2.12# | 0 | 0.22 | 0.125 | 0.81 | 1.36 | 0.48 |
| P | 1.44* | 1.94* | 1.00* | 4.00+ | 2.12# | 0 | 0.22 | 0.125 | 0.81 | 1.00 | 0.48 |
| Q | 1.44* | 1.94* | 1.00* | 4.00+ | 2.12# | 0 | 0.33 | 0.125 | 0.81 | 1.36 | 0.48 |

*Calcium salt of keto-analog
+Sodium salt of keto-analog
Calcium salt of hydroxy-analog Approximately 10 grams of the five analogs and three grams of amino acids were given three times a day as a powder or in gelatin capsules with meals. All nine (or 10) constituents of the mixture were contained in each dose. Protein intake was restricted to either 1.0 or 0.75 gm/kg per day. Following a control period, a keto acid mixture similar in composition to that earlier employed was administered. As before, plasma ammonia again fell, though not to normal. Withdrawal of this supplement was again followed by a rise in plasma ammonia. Resumption of similar therapy (mixtures G and H) failed to reduce plasma ammonia. At this point, it became apparent that plasma lysine, histidine and arginine had fallen to subnormal levels evidently due to inadequate N intake.

Subsequently, these amino acids plus threonine and tryptophan were added to the mixes (I through Q). At the same time, protein intake was reduced to 0.75 gm/kg per day. Over the next 3 weeks, plasma ammonia fell to normal concurrent with the restoration of normal or nearly normal plasma levels of lysine, histidine and arginine.

Alterations in the composition of the nutritional supplement were made chiefly in response to abnormalities in levels of amino acids and ammonia in plasma. Late in the study, histidine was noted to be still subnormal and the amount of this amino acid was increased (mixture Q).

One of the keto analogs which was frequently changed was isoleucine (mixtures H, J, K and P). We were initially concerned about plasma levels of alloisoleucine which were as high or higher than that of isoleucine. The appearance of alloisoleucine reflects racemization of alpha-keto-beta-methylvaleric acid (the keto analog of isoleucine) with subsequent transamination to yield both isoleucine and alloisoleucine. To evaluate the possibility that alloisoleucine was being incorporated into protein, plasma was obtained after 6 months of therapy and protein was precipitated, washed and hydrolyzed to its constituent amino acids. Plasma protein from a healthy adult was used as control. The ratios of alloisoleucine to isoleucine were 0.022 and 0.020, respectively. Pure isoleucine, when subjected to the same hydrolysis conditions, also yielded 2% alloisoleucine.

These results indicated that alloisoleucine was not incorporated into protein, and hence we continued to attempt to normalize plasma isoleucine without regard to the concentration of alloisoleucine.

Upon observation that there were subnormal levels of arginine, the quantity of this component was increased (mixture O). Plasma alanine fell, but there was little change in glutamine or ammonia. In mixture P, modest reductions were made in both the isoleucine analog and arginine dosage. At the same time, the caloric intake was increased by adding a high carbohydrate beverage. These changes resulted in improvement in ammonia, glutamine and alanine. Histidine dosage was increased in mixture P as we have heretofore noted. In subsequent stages of the treatment during a 3 months period of therapy, ammonia and alanine were at the range of normal and glutamine near normal.

As a result of the treatment, significant development in the patient's psychological and physical condition were noted. The child appeared to be more alert and more responsive to her environment. She continued to increase in height at the same rate as before therapy despite protein restriction. There was also some weight gain especially during the latter part of the treatment. Nitrogen intake was higher during the treatment period owing to the nitrogen content of the added essential amino acids and the increased number of gelatin capsules consumed. Despite the increase in nitrogen intake, there was no change in the urinary nitrogen output. The additional nitrogen, 0.8 gm/day appeared to have been wholly retained. These data suggest that nitrogen balance improved.

In the previous study, when keto acids alone were first administered, there was a fall in plasma levels of arginine (the synthesis of which is perhaps limited in this child) and of those essential amino acids not supplied as keto analogs. This was associated with a rise of ammonia to abnormal levels. We inferred that protein synthesis had become limited by deficiencies of these essential amino acids and that increased blood ammonia reflected decreased utilization of the administered keto acids. Subsequently when these other essential amino acids and arginine were added to the mixture, there was a prompt rise in the respective blood amino acids and a progressive fall in ammonia to nearly normal levels.

During therapy, we found no evidence of nausea, vomiting, diarrhea, lethargy or acidosis.

The effectiveness of nutritional supplements with keto and hydroxy acids and essential amino acids was substantiated by withdrawl of these from the patient, which led to a prompt rise in ammonia, glutamine and alanine to abnormal levels. These returned towards normal when the nutritional supplements were reinstituted. Indirect evidence based on nitrogen intake and urinary nitrogen output shows increased retention of nitrogen on keto and/or hydroxy acid therapy, suggesting improved nitrogen balance. This information is supported by urinary partition of nitrogen which shows no increase in urea excretion despite an increased nitrogen intake on therapy.

In addition to this nitrogen-sparing effect, there is some evidence that the administered analogs have led to improved protein tolerance. We have been able to increase the patient's nitrogen intake from 2.8 gm/day used in our initial study to 4.6 gm/day without losing positive nitrogen balance or precipitating hyperammonemia. We have observed no essential difference in attained results whether the hydroxy analog or the keto analog of methionine was employed.

The mixture reported in Table IX contained a high proportion of the keto analog of phenlalanine. The comparatively high proportion of this compound is not generally required but was used in this instance because the patient had a peculiar defect in the metabolism of this amino acid. Mixtures recommended for more general use in the treatment by congenital hyperammonemia are set out below.

Another type of congenital hepatic disorder attributed to inborn error in amino acid metabolism is citrullinemia, in which there is a deficiency in argino-succinic acid synthetase in the liver. In this condition, there is manifested an excessive amount of citrulline in blood, urine and cerebrospinal fluid, and ammonia intoxication. In a number of previous reported cases of lethal neonatal citrullinemia death ensued at a mean age of 5.2 days.

A 20 day old infant diagnosed as suffering from neonatal citrullinemia showed a plasma citrulline of 67.7 mg%. Intravenous infusion of a mixture of the alpha-keto analogs of valine, leucine, isoleucine, phenylalanine and methionine, produced a 2-fold (leucine) to a 24-fold (methionine) increase in the corresponding amino acids, thus demonstrating effective transamination.

The infant was then placed on oral administration of a mixture of the alpha keto analogs of the first four of the above-named amino acids and the racemic alpha hydroxy analog of methionine, supplemented with prepared formula and lipid to a total of 120 cal/kg/day and 0.5 grams protein/kg/day. Blood ammonia declined from initial values between 412 and 943 $\mu$g% to 44 $\mu$g% and citrulline was reduced to 14.2 mg%. Weight gain was established and all abnormal neurological signs resolved. At 45 days, the patient's clinical and biochemical condition showed marked improvement, indicating the use of these analogs of essential amino acids to be an effective mode of therapy in this condition.

In general, for the effective treatment of congenital hyperammonemia in children, the dosages tabulated below are recommended for intravenous administration:

|  | grams |
| --- | --- |
| Keto-valine | 0.9 (Na or Ca salt) |
| Keto-leucine | 1.2 (Na or Ca salt) |
| Keto-isoleucine | 0.8 (Na or Ca salt) |
| Keto or hydroxy methionine | 1.2 (Na or Ca salt) |
| Phenylpyruvate or lactate | 1.2 (Na or Ca salt) |
| Histidine | 0.2 |
| Threonine | 0.2 |
| Tryptophan | 0.1 |
| Lysine hydrochloride | 0.3 |
| Arginine hydrochloride | 2.0 |

The foregoing mixture can be intravenously administered in a period of 3 to 4 hours in a newborn infant of normal body weight (6 to 7 pounds; ~2.7 to 3.2 kgs).

For oral usage in congenital hyperammonemia in infants of about such weight, the recommended daily dosage is:

|  | grams |
| --- | --- |
| Keto-valine | 0.68 (Na or Ca salt) |
| Keto-leucine | 0.94 (Na or CA salt) |
| Keto-isoleucine | 0.69 (Na or Ca salt) |
| L-phenyl lactate or Phenylpyruvate | 0.47 (Na or Ca salt) |
| Keto or hydroxy methionine | 0.50 (Na or Ca salt) |
| Lysine hydrochloride | 0.20 |

| | grams |
|---|---|
| Histidine | 0.12 |
| Threonine | 0.15 |
| Tryptophan | 0.10 |
| Arginine hydrochloride | 1.0 |

The dosage for oral administration, it will be observed, is considerably smaller than that indicated above for intravenous use, because the latter is generally employed in emergency situations while oral ingestion is utilized for maintenance therapy in long term growth and usually in conjunction with some dietary protein.

The foregoing dosages, as indicated, are intended for infants. For larger children, the oral and intravenous doses are increased with relation to their height and weight (surface area). These mixtures are recommended for use in children with defects in any of the five known urea cycle enzyme defects with the exception of that due to arginase deficiency. In the latter condition, arginine accumulates in the plasma, so that arginine is excluded from the mixture. In some instances, effective treatment is obtained by oral or intravenous administration of only the calcium salts of the keto analogs of the branched chain amino acids.

Treatment of Protein Depletion

Protein deficiency usually occurs due to the low bioavailability of dietary protein or increased nitrogen losses. The object of the embodiment of the invention now described is to reduce the exogenous protein requirement of an individual in such a manner that protein is actually conserved in the body. Generally, the composition of matter employed in this embodiment of the invention may be that described previously relative to the treatment of renal disorders. This mixture can be given orally or intravenously, if necessary.

It can be shown that administration of this embodiment of the present composition of matter diverts nitrogenous precursors of urea away from urea formation due to the utilization of said precursors in the formation of amino acids as previously described. This treatment leads to an alteration of the body's metabolic machinery such that urea formation, and therefore protein requirement, is reduced even for a period of time after treatment has been discontinued. Thus, individuals so treated are made more capable of conserving protein as a result of treatment according to the invention. Although protein may still be lost from the body, the body's ability to conserve protein is increased, thereby reducing exogenous protein requirements.

Administration of combinations of hydroxy-acid analogs with alpha-keto-acids and/or certain of the amino acids themselves, when used in concert with low protein diets, causes a substantial reduction in nitrogen excretion here measured as urea, thereby indicating that the body's mechanisms for conserving protein are altered to enable the body to more efficiently conserve protein. Thus, the mechanism by which the nitrogen conservation is promoted in the treatment of the several disorders described herein is not simply by means of conversion of the analogs to the corresponding amino acids. While nitrogen conservation is facilitated by restoration of carbon skeletons lost by degradation, metabolic pathways are also altered which allow more efficient utilization of the analogs in the body.

In treatment of the disorders described herein, it has been shown that administration of the present compositions of matter allow patients to attain nitrogen balance, (thus, maintenance of tissue protein), a condition not easily obtainable with treatment by amino acids alone or by dietary protein intake, especially when conditions of excessive protein wastage are present.

A daily dosage of a particular mixture of hydroxy-acids, keto-acids, and amino acids which has proven effective in restoring nitrogen balance to patients who had been losing tissue protein comprises:

Table X

| Quantity | Substance |
|---|---|
| 2.9 grams | alpha-keto-acid analog of valine; sodium or calcium salt |
| 4.0 grams | alpha-keto-acid analog of leucine; sodium or calcium salt |
| 2.9 grams | L-hydroxy analog of isoleucine; sodium or calcium salt |
| 2.1 grams | D,L-hydroxy analog of methionine; sodium or calcium salt |
| 2.0 grams | L-hydroxy analog of phenylalanine; sodium or calcium salt |
| ~.5 grams | L-histidine |
| ~.7 gram | L-threonine |
| ~.3 gram | L-tryptophan |
| ~.8 gram | L-lysine hydrochloride |

This mixture is relatively inexpensive, is stable, and particularly palatable for daily oral administration. This mixture and other embodiments of the present compositions of matter may be used in protein deficient diets and conditions which have been previously believed best correctable by protein intake. Protein administration increases nitrogen losses and must be given in large quantities to counter these losses. A positive protein balance is thus difficult to achieve. Prevention of nitrogen losses from the body is therefore desirable and is desirable not only in instances of malnutrition, but also in wasting diseases, or conditions such as cancer, chronic infection, burns, surgery, trauma, diabetes, or other conditions characterized by tissue wastage. Nitrogen balance is presently restored by oral or parenteral administration of the present compositions of matter by "turning off" nitrogen wastage from the body. As long as low nitrogen intake is maintained, prevention of nitrogen leakage from the body's metabolic pool occurs.

The mechanism by which nitrogen is conserved is likely accomplished by diminution of certain amino acids in the blood, particularly alanine. The concentration of alanine is reduced by reaction in muscle tissue between the keto-acid analogs, particularly those of valine, leucine, and isoleucine, with alanine, this reduction in alanine concentration causing reduced production of urea in the liver. It can also be seen from the teachings provided herein that polymers such as the glycolides and lactides, of the respective hydroxy acids which are convertable by intact body tissue to the corresponding alpha-keto-acid analogs are also capable of use in the invention.

What is claimed is:.

1. A composition capable of promoting protein synthesis and conserving nitrogen in a patient in need thereof, said composition being in the form of a mixture adapted for oral or parenteral administration to subjects on a protein-restricted diet, said composition being substantially devoid of non-essential amino acids, and said composition comprising a mixture of effective quantities of hydroxy-acid and/or keto-acid analogs of the essential amino acids valine, phenylalanine, isoleucine, leucine and methionine, at least one of said analogs of essential amino acids being hydroxy-acid analogs, said hydroxy-acid or keto-acid analogs being present in the form of the acid analogs per se or salts of the acid analogs.

2. A composition as defined in claim 1 wherein the hydroxy-acid analogs are present as the L-hydroxy form, except the hydroxy-acid analog of methionine which is present as the D, L-form.

3. A composition as defined in claim 1 wherein the mixture does not contain both the hydroxy-acid analog and the keto-acid analog of the same essential amino acid.

4. A composition as defined in claim 1 containing the hydroxy-acid analogs of methionine, phenylalanine and isoleucine and the keto-acid analogs of valine and leucine.

5. A composition as defined in claim 1 wherein said analogs are present as calcium or sodium salts of the acid analogs.

6. A composition as defined in claim 5 wherein said composition also contains in effective quantities in amino acid form L-lysine hydrochloride or acetate, L-threonine and L-tryptophan.

7. A composition as defined in claim 6 further containing in effective quantity L-histidine.

8. A composition as defined in claim 6 further containing in effective quantity L-arginine.

9. A composition as defined in claim 1 wherein the recited analogs are present in amounts to afford dosages constituting at least the minimum daily requirement of the corresponding essential amino acid.

10. A composition as defined in claim 1 wherein the quantities of the analogs of valine, leucine and isoleucine are each present in approximately 2 to 3 times that of phenylalanine and methionine.

11. A composition as defined in claim 1 wherein tryptophan is also present in effective quantity in the form of its alpha-keto acid analog.

12. A composition as defined in claim 1 wherein histidine is also present in effective quantity in the form of its alpha-keto acid analog.

13. A composition as defined in claim 1 wherein the five recited analogs are present as salts in the weight proportions: 2 to 4 parts valine analog, 3 to 5 parts leucine analog, 2.5 to 3.5 parts isoleucine analog, 1.5 to 2.5 parts each of methionine analog and phenylalanine analog.

14. A composition as defined in claim 13 wherein said components are present in a sterilized isotonic aqueous solution for parenteral administration.

15. A composition for treatment of uremia resulting from renal disorders comprising a mixture in form for oral or parenteral administration to subjects on a protein-restricted diet, said composition consisting essentially of the components in the following ranges of proportions by weight:
   1.5–2.5 parts sodium or calcium phenylpyruvate;
   2.0–4.0 parts sodium or calcium alpha-keto isovalerate;
   3.0–5.0 parts sodium or calcium alpha-keto-isocaproate;
   1.5–2.5 parts sodium or calcium D,L-alpha-hydroxy-gamma-methyl-thiobutyrate;
   2.5–3.5 parts racemic sodium or calcium alpha-keto-beta-methylvalerate;
   about 0.5 parts of L-histidine;
   about 0.8 parts of L-lysine hydrochloride or acetate;
   about 0.5 parts of L-threonine;
   about 0.25 parts of L-tryptophan.

16. A composition for treatment of uremia resulting from renal disorders comprising a mixture in form for oral or parenteral administration to subjects on a protein-restricted diet, said composition consisting essentially of the components in the following ranges of proportions by weight:
   1.5–2.5 parts sodium or calcium L-phenyllacetate;
   2.0–4.0 parts sodium or calcium alpha-keto isovalerate;
   2.5–3.5 parts sodium or calcium alpha keto or L-alpha hydroxy-beta-methylvalerate;
   3.0–5.0 parts sodium or calcium alpha-keto-isocaproate;
   1.5–2.5 parts sodium or calcium D,L-alpha-hydroxy-gamma-methyl-thiobutyrate;
   about 0.5 parts of L-histidine;
   about 0.8 parts of L-lysine hydrochloride or acetate;
   about 0.5 parts of L-threonine;
   about 0.25 parts of L-tryptophan.

17. A method for promoting protein synthesis and conserving nitrogen in a patient in need thereof which method comprises orally or parenterally administering in effective dosages to subjects on a protein-restricted diet a composition substantially devoid of non-essential amino acids, said composition comprising a mixture of effective quantities of hydroxy-acid and/or keto-acid analogs of the essential amino acids valine, phenylalanine, isoleucine, leucine and methionine, at least one of said analogs of essential amino acids being hydroxy-acid analogs, said hydroxy-acid or keto-acid analogs being present in the form of the acid analogs per se or salts of the acid analogs.

18. A method as defined in claim 17 wherein said composition also contains in effective quantities in amino form: L-lysine hydrochloride or acetate, L-threonine and L-tryptophan.

19. A method as defined in claim 18 wherein said composition also contains in effective quantity in amino acid form L-histidine.

20. A method as defined in claim 18 wherein said composition also contains in effective quantity L-arginine.

21. A method as defined in claim 17 wherein the recited analogs are present in said composition in amounts to afford dosages constituting at least the minimum daily requirement of the corresponding essential amino acid.

22. A method as defined in claim 17 wherein the quantities of the analogs of valine, leucine and isoleucine are each present in said composition in approximately two to three times that of phenylalanine and methionine.

23. A method as defined in claim 17 wherein the five recited analogs are present in the weight proportions: 2 to 4 parts valine analog, 3 to 5 parts leucine analog, 2.5 to 3.5 parts isoleucine analog, 1.5 to 2.5 parts each of the analogs of methionine and phenylalanine.

24. A method as defined in claim 17 wherein said composition is parenterally administered as a sterilized isotonic aqueous solution.

25. A method for treatment of uremia resulting from renal disorders which comprises oral or parenteral administration in effective dosages to a subject on a diet of restricted amounts of protein of a therapeutic composition substantially devoid of non-essential amino acid;

said composition consisting essentially of the components in the following ranges of proportions by weight:
- 1.5–2.5 parts sodium or calcium phenylpyruvate;
- 2.0–4.0 parts sodium or calcium alpha-keto isovalerate;
- 3.0–5.0 parts sodium or calcium alpha-keto-isocaproate;
- 1.5–2.5 parts sodium or calcium D,L-alpha-hydroxy-gamma-methyl-thiobutyrate;
- 2.5–3.5 parts sodium or calcium racemic alpha-keto-beta methylvalerate;
- about 0.5 parts of L-histidine;
- about 0.8 parts of L-lysine hydrochloride or acetate;
- about 0.5 parts of L-threonine;
- about 0.25 parts of L-tryptophan.

26. The method as defined in claim 25 wherein the defined composition is intravenously administered to patients suffering from severe uremic syndrome for the purpose of diminishing the rate of urea formation in the liver of such patients.

27. The method as defined in claim 25 wherein the defined composition is orally administered.

28. A method for treatment of uremia resulting from renal disorders which comprises oral or parenteral administration in effective dosages to a subject on a diet of restricted amounts of protein or a therapeutic composition substantially devoid of non-essential amino acid; said composition consisting essentially of the components in the following ranges of proportions by weight:
- 1.5–2.5 parts sodium or calcium phenyllactate;
- 2.0–4.0 parts sodium or calcium alpha-keto-isovalerate;
- 3.0–5.0 parts sodium or calcium alpha-keto-isocaproate;
- 1.5–2.5 parts sodium or calcium D,L-alpha-hydroxy-gamma-methyl-thiobutyrate;
- 2.5–3.5 parts L-(R,S)-alpha-hydroxy- or R,S-alpha-keto-beta-methylvalerate;
- about 0.5 parts of L-histidine;
- about 0.8 parts of L-lysine hydrochloride or acetate;
- about 0.5 parts of L-threonine;
- about 0.25 parts of L-tryptophan.

29. The method as defined in claim 28 wherein the defined composition is intravenously administered.

30. The method as defined in claim 28 wherein the defined composition is orally administered.

* * * * *